(12) United States Patent
Wubbeling et al.

(10) Patent No.: US 10,369,032 B2
(45) Date of Patent: *Aug. 6, 2019

(54) TRANSLUMINAL DELIVERY SYSTEM

(71) Applicant: C. R. Bard, Inc., Murray Hill, NJ (US)

(72) Inventors: Martin Wubbeling, Mannheim (DE); Daniel Dietrich, Karlsruhe (DE); Erhard Elsasser, Pfintzal/Berghausen (DE); Beate Walter, Stutensee (DE)

(73) Assignee: C. R. Bard, Inc., Murray Hill, NJ (US)

( * ) Notice: Subject to any disclaimer, the term of this patent is extended or adjusted under 35 U.S.C. 154(b) by 416 days.

This patent is subject to a terminal disclaimer.

(21) Appl. No.: 14/555,849

(22) Filed: Nov. 28, 2014

(65) Prior Publication Data

US 2015/0088242 A1 Mar. 26, 2015

Related U.S. Application Data

(63) Continuation of application No. 13/322,908, filed as application No. PCT/EP2010/057401 on May 28, 2010, now Pat. No. 8,920,484.

(Continued)

(30) Foreign Application Priority Data

May 29, 2009 (GB) .................................. 0909319.6

(51) Int. Cl.
*A61F 2/966* (2013.01)
*A61F 2/95* (2013.01)

(52) U.S. Cl.
CPC ................ *A61F 2/966* (2013.01); *A61F 2/95* (2013.01); *A61F 2002/9665* (2013.01);
(Continued)

(58) Field of Classification Search
CPC ................ A61F 2/95; A61F 2/962–966; A61F 2002/9665; A61F 2002/9583; A61F 2002/9505–9511
See application file for complete search history.

(56) References Cited

U.S. PATENT DOCUMENTS

| 4,576,534 A | 3/1986 | Barth et al. |
| 4,580,568 A | 4/1986 | Gianturco |

(Continued)

FOREIGN PATENT DOCUMENTS

| CA | 2537366 A1 | 4/2005 |
| DE | 10016920 A1 | 10/2001 |

(Continued)

OTHER PUBLICATIONS

CA 2,523,557 filed Apr. 28, 2004 Offical Action dated Aug. 20, 2010.
(Continued)

*Primary Examiner* — Shaun David
(74) *Attorney, Agent, or Firm* — Rutan & Tucker, LLP

(57) ABSTRACT

A transluminal delivery system and a method of assembling. The system includes a cylindrical, inner-catheter component and a retractable sheath surrounding the component and defining a space between the component and the sheath to receive a self-expanding luminal prosthesis between the component and the sheath. The inner-catheter component may include at least one sleeve having fibers, at least one connected sleeve portion connected to the inner catheter, and at least one unconnected sleeve portion slidably engaging the inner catheter such that when the sheath retracts, the unconnected portion expands and sleeve fibers engage the prosthesis's luminal surface, wherein the engagement opposes proximal stent movement.

20 Claims, 4 Drawing Sheets

Related U.S. Application Data

(60) Provisional application No. 61/182,263, filed on May 29, 2009.

(52) U.S. Cl.
CPC ............... *A61F 2210/0057* (2013.01); *A61F 2220/0025* (2013.01); *Y10T 29/49863* (2015.01)

(56) References Cited

U.S. PATENT DOCUMENTS

| | | |
|---|---|---|
| 4,719,853 A | 1/1988 | Bowers |
| 4,762,128 A | 8/1988 | Rosenbluth |
| 4,768,507 A | 9/1988 | Fischell et al. |
| 4,950,227 A | 8/1990 | Savin et al. |
| 5,026,377 A * | 6/1991 | Burton .................. A61F 2/82 606/108 |
| 5,037,427 A | 8/1991 | Harada et al. |
| 5,201,757 A | 4/1993 | Heyn et al. |
| 5,201,901 A | 4/1993 | Harada et al. |
| 5,445,646 A | 8/1995 | Euteneuer et al. |
| 5,458,605 A | 10/1995 | Klemm |
| 5,474,563 A | 12/1995 | Myler et al. |
| 5,480,423 A | 1/1996 | Ravenscroft et al. |
| 5,484,444 A | 1/1996 | Braunschweiler et al. |
| 5,520,645 A | 5/1996 | Imran et al. |
| 5,554,181 A | 9/1996 | Das |
| 5,562,641 A | 10/1996 | Flomenblit et al. |
| 5,562,726 A | 10/1996 | Chuter |
| 5,569,295 A | 10/1996 | Lam |
| 5,569,296 A | 10/1996 | Marin et al. |
| 5,591,222 A | 1/1997 | Susawa et al. |
| 5,609,627 A | 3/1997 | Goicoechea et al. |
| 5,619,878 A | 4/1997 | Grosjean et al. |
| 5,645,559 A | 7/1997 | Hachtman et al. |
| 5,683,451 A | 11/1997 | Lenker et al. |
| 5,690,643 A | 11/1997 | Wijay |
| 5,697,948 A | 12/1997 | Marin et al. |
| 5,700,269 A | 12/1997 | Pinchuk et al. |
| 5,702,418 A | 12/1997 | Ravenscroft |
| 5,709,703 A | 1/1998 | Lukic et al. |
| 5,749,880 A | 5/1998 | Banas et al. |
| 5,749,921 A | 5/1998 | Lenker et al. |
| 5,755,777 A | 5/1998 | Chuter |
| 5,776,141 A | 7/1998 | Klein et al. |
| 5,807,327 A | 9/1998 | Green et al. |
| 5,824,040 A | 10/1998 | Cox et al. |
| 5,824,041 A | 10/1998 | Lenker et al. |
| 5,843,161 A * | 12/1998 | Solovay .................. A61F 2/07 623/1.13 |
| 5,843,167 A | 12/1998 | Dwyer et al. |
| 5,876,448 A | 3/1999 | Thompson et al. |
| 5,902,334 A | 5/1999 | Dwyer et al. |
| 5,913,871 A | 6/1999 | Werneth et al. |
| 5,920,975 A | 7/1999 | Morales |
| 5,928,258 A | 7/1999 | Khan et al. |
| 5,968,068 A | 10/1999 | Dehdashtian et al. |
| 5,980,532 A | 11/1999 | Wang |
| 5,980,548 A | 11/1999 | Evans et al. |
| 5,989,280 A | 11/1999 | Euteneuer et al. |
| 6,033,388 A | 3/2000 | Nordstrom et al. |
| 6,048,350 A | 4/2000 | Vrba |
| 6,056,906 A | 5/2000 | Werneth et al. |
| 6,063,092 A | 5/2000 | Shin |
| 6,077,295 A | 6/2000 | Limon et al. |
| 6,110,142 A | 8/2000 | Pinchuk et al. |
| 6,110,180 A | 8/2000 | Foreman et al. |
| 6,110,191 A | 8/2000 | Dehdashtian et al. |
| 6,113,628 A | 9/2000 | Borghi et al. |
| 6,123,712 A | 9/2000 | Di Caprio et al. |
| 6,132,458 A | 10/2000 | Staehle et al. |
| 6,143,014 A | 11/2000 | Dehdashtian et al. |
| 6,203,568 B1 | 3/2001 | Lombardi et al. |
| 6,210,429 B1 | 4/2001 | Vardi et al. |
| 6,214,039 B1 | 4/2001 | Banas et al. |
| 6,245,099 B1 | 6/2001 | Edwin et al. |
| 6,248,112 B1 * | 6/2001 | Gambale ............ A61B 17/3468 606/108 |
| 6,258,099 B1 | 7/2001 | Mareiro et al. |
| 6,302,893 B1 | 10/2001 | Limon et al. |
| 6,302,906 B1 | 10/2001 | Goicoechea et al. |
| 6,306,162 B1 | 10/2001 | Patel |
| 6,319,275 B1 | 11/2001 | Lashinski et al. |
| 6,322,586 B1 | 11/2001 | Monroe et al. |
| 6,352,531 B1 | 3/2002 | O'Connor et al. |
| 6,451,047 B2 | 9/2002 | McCrea et al. |
| 6,471,718 B1 | 10/2002 | Staehle et al. |
| 6,500,202 B1 | 12/2002 | Shaolian et al. |
| 6,576,006 B2 | 6/2003 | Limon et al. |
| 6,607,551 B1 | 8/2003 | Sullivan et al. |
| 6,613,075 B1 | 9/2003 | Healy et al. |
| 6,620,172 B1 | 9/2003 | Dretler et al. |
| 6,620,191 B1 | 9/2003 | Svensson |
| 6,758,858 B2 | 7/2004 | McCrea et al. |
| 6,776,791 B1 | 8/2004 | Stallings et al. |
| 6,796,998 B2 | 9/2004 | Schaldach et al. |
| 6,858,034 B1 | 2/2005 | Hijlkema et al. |
| 6,945,989 B1 | 9/2005 | Betelia et al. |
| 7,011,675 B2 | 3/2006 | Hemerick et al. |
| 7,172,618 B2 | 2/2007 | Lupton |
| 7,241,308 B2 | 7/2007 | Andreas et al. |
| 7,473,271 B2 | 1/2009 | Gunderson |
| 7,717,949 B2 | 5/2010 | Dorn |
| 7,867,267 B2 | 1/2011 | Sullivan et al. |
| 8,287,582 B2 | 10/2012 | Dorn |
| 8,679,172 B2 | 3/2014 | Dorn et al. |
| 2001/0001833 A1 | 5/2001 | Ravenscroft et al. |
| 2001/0007082 A1 | 7/2001 | Dusbabek et al. |
| 2001/0032009 A1 | 10/2001 | Layne et al. |
| 2001/0039446 A1 | 11/2001 | Edwin et al. |
| 2001/0049549 A1 | 12/2001 | Boylan et al. |
| 2002/0029076 A1 | 3/2002 | Yee |
| 2002/0038143 A1 | 3/2002 | McCrea et al. |
| 2002/0058993 A1 | 5/2002 | Landau et al. |
| 2002/0099435 A1 | 7/2002 | Stinson |
| 2002/0138966 A1 | 10/2002 | Motsenbocker |
| 2002/0147490 A1 | 10/2002 | Pletzer et al. |
| 2002/0156516 A1 | 10/2002 | Vardi et al. |
| 2002/0193863 A1 | 12/2002 | Rourke et al. |
| 2003/0032999 A1 | 2/2003 | Huang |
| 2003/0153969 A1 | 8/2003 | Dehdashtian et al. |
| 2004/0106977 A1 | 6/2004 | Sullivan et al. |
| 2004/0143272 A1 | 7/2004 | Cully et al. |
| 2004/0167511 A1 * | 8/2004 | Buehlmann ........ A61B 18/1492 606/45 |
| 2004/0204749 A1 | 10/2004 | Gunderson |
| 2005/0049608 A1 * | 3/2005 | Aznoian .................. A61F 2/94 606/108 |
| 2005/0055077 A1 * | 3/2005 | Marco ............ A61B 17/320725 623/1.11 |
| 2006/0184225 A1 | 8/2006 | Pryor |
| 2006/0184226 A1 | 8/2006 | Austin |
| 2006/0216404 A1 | 9/2006 | Seyler et al. |
| 2006/0259123 A1 | 11/2006 | Dorn |
| 2006/0276873 A1 | 12/2006 | Sato |
| 2007/0024072 A1 | 2/2007 | Leon |
| 2007/0043430 A1 | 2/2007 | Stinson |
| 2007/0083256 A1 | 4/2007 | Dorn |
| 2007/0156251 A1 | 7/2007 | Karmon |
| 2007/0191925 A1 | 8/2007 | Dorn |
| 2008/0051867 A1 | 2/2008 | Davila et al. |
| 2009/0177264 A1 | 7/2009 | Ravenscroft |
| 2010/0070016 A1 | 3/2010 | Dorn et al. |
| 2012/0059449 A1 | 3/2012 | Dorn et al. |
| 2012/0143304 A1 | 6/2012 | Wubbeling et al. |
| 2013/0079863 A1 | 3/2013 | Dorn |

FOREIGN PATENT DOCUMENTS

| | | |
|---|---|---|
| DE | 10212707 A1 | 10/2003 |
| DE | 20306823 U1 | 11/2003 |
| EP | 0596145 A1 | 5/1994 |

(56) References Cited

FOREIGN PATENT DOCUMENTS

| | | | |
|---|---|---|---|
| EP | 0775470 | A1 | 5/1997 |
| EP | 0788332 | | 8/1997 |
| EP | 0826346 | | 3/1998 |
| EP | 0834293 | A1 | 4/1998 |
| EP | 0836447 | A2 | 4/1998 |
| EP | 0873731 | | 10/1998 |
| EP | 0943300 | A1 | 9/1999 |
| EP | 1382367 | A1 | 1/2004 |
| EP | 1466570 | A1 | 10/2004 |
| EP | 1803423 | A3 | 6/2009 |
| FR | 2742042 | A1 | 6/1997 |
| FR | 2760351 | A1 | 9/1998 |
| JP | 08-141090 | A | 6/1996 |
| JP | 11-512318 | T | 10/1999 |
| JP | 2001-501115 | A | 1/2001 |
| JP | 2002-501404 | A | 1/2002 |
| JP | 2003-500103 | A | 1/2003 |
| JP | 2003-500104 | A | 1/2003 |
| JP | 2005-038367 | A | 2/2005 |
| JP | 2007-024072 | A | 2/2007 |
| JP | 2008-508937 | A | 3/2008 |
| WO | 1995033422 | A1 | 12/1995 |
| WO | 1996028115 | A1 | 9/1996 |
| WO | 1996039998 | A2 | 12/1996 |
| WO | 1997009932 | A1 | 3/1997 |
| WO | 1998014233 | A1 | 4/1998 |
| WO | 1998031305 | A1 | 7/1998 |
| WO | 1998053761 | A1 | 12/1998 |
| WO | 1999055255 | | 11/1999 |
| WO | 2000012030 | A9 | 10/2000 |
| WO | 2000071057 | A1 | 11/2000 |
| WO | 2000071058 | A1 | 11/2000 |
| WO | 2001005331 | | 1/2001 |
| WO | 2001021103 | A2 | 3/2001 |
| WO | 2001034061 | A1 | 5/2001 |
| WO | 2002015820 | A2 | 2/2002 |
| WO | 2003003944 | A2 | 1/2003 |
| WO | 2003024362 | A1 | 3/2003 |
| WO | 2003049641 | A1 | 6/2003 |
| WO | 2004062458 | A2 | 7/2004 |
| WO | 2004096091 | A1 | 11/2004 |
| WO | 2004096091 | A8 | 3/2005 |
| WO | 2004110521 | A3 | 3/2005 |
| WO | 2005030092 | A3 | 7/2005 |
| WO | 2005053574 | A3 | 2/2006 |
| WO | 2006020028 | A1 | 2/2006 |
| WO | 2006026377 | A1 | 3/2006 |
| WO | 2007149464 | A2 | 12/2007 |
| WO | 2009033066 | A1 | 3/2009 |
| WO | 2010086320 | A1 | 8/2010 |
| WO | 2010136558 | A1 | 12/2010 |

OTHER PUBLICATIONS

GB 0901496.0 Search Report dated Apr. 28, 2009.
JP 2006-505303 filed Feb. 16, 2006 Office Action dated Mar. 23, 2010.
JP 2006-527350 Examination Report (translated) dated Aug. 6, 2009.
JP 2011-546827 Office Action (translated) dated Sep. 20, 2013.
PCT/EP2004/004486 filed Apr. 28, 2004 International Preliminary Report on Patentability dated Oct. 28, 2005.
PCT/EP2004/004486 filed Apr. 28, 2004 Search Report dated Sep. 27, 2004.
PCT/EP2004/004486 filed Apr. 28, 2004 Written Opinion dated Sep. 27, 2004.
PCT/EP2009/061918 filed Sep. 5, 2009 Search Report dated Nov. 25, 2009.
PCT/EP2009/061918 filed Sep. 15, 2009 Written Opinion dated Nov. 25, 2009.
PCT/EP2010/050910 filed Jan. 27, 2010 International Preliminary Report on Patentability dated Aug. 2, 2011 and Written Opinion dated Mar. 30, 2010.
PCT/EP2010/050910 filed Jan. 27, 2010 International Search Report dated Mar. 30, 2010.
PCT/EP2010/057401 filed May 28, 2010 International Preliminary Report on Patentability dated Sep. 16, 2011.
PCT/EP2010/057401 filed May 28, 2010 International Search Report dated Aug. 9, 2010.
PCT/EP2010/057401 filed May 28, 2010 Written Opinion dated Aug. 9, 2010.
PCT/US2000/014038 filed May 19, 2000 International Preliminary Examination Report dated Jul. 31, 2001.
PCT/US2000/014038 filed May 19, 2000 Search Report dated Sep. 13, 2000.
U.S. Appl. No. 10/552,886, filed Nov. 18, 2005 Non-Final Office Action dated Sep. 28, 2007.
U.S. Appl. No. 10/552,886, filed Nov. 18, 2005 Final Office Action dated Oct. 29, 2008.
U.S. Appl. No. 10/552,886, filed Nov. 18, 2005 Non-Final Office Action dated Apr. 2, 2008.
U.S. Appl. No. 10/552,886, filed Nov. 18, 2005 Non-Final Office Action dated Sep. 8, 2007.
U.S. Appl. No. 10/552,886, filed Nov. 18, 2005 Decision on Appeal dated Jan. 11, 2012.
U.S. Appl. No. 10/552,886, filed Nov. 18, 2005 Notice of Allowance dated May 18, 2012.
U.S. Appl. No. 10/572,191, filed Apr. 11, 2006 Advisory Action dated Jan. 2, 2009.
U.S. Appl. No. 10/572,191, filed Apr. 11, 2006 Final Office Action dated Jun. 8, 2009.
U.S. Appl. No. 10/572,191, filed Apr. 11, 2006 Final Office Action dated Oct. 10, 2008.
U.S. Appl. No. 10/572,191, filed Apr. 11, 2006 Final Office Action dated Oct. 5, 2009.
U.S. Appl. No. 10/572,191, filed Apr. 11, 2006 Non-Final Office Action dated Mar. 25, 2008.
U.S. Appl. No. 12/560,295, filed Sep. 15, 2009 Final Office Action dated Feb. 15, 2013.
U.S. Appl. No. 12/560,295, filed Sep. 15, 2009 Non-Final Office Action dated Oct. 26, 2012.
U.S. Appl. No. 13/147,120, filed Jul. 29, 2011 Non-Final Office Action dated Mar. 19, 2013.
U.S. Appl. No. 13/147,120, filed Jul. 29, 2011 Notice of Allowance dated Aug. 6, 2013.
U.S. Appl. No. 13/322,908, filed Nov. 28, 2011 Notice of Allowance dated Sep. 12, 2014.

\* cited by examiner

TRANSLUMINAL DELIVERY SYSTEM

PRIORITY

This application is a continuation of U.S. patent application Ser. No. 13/322,908, filed Feb. 3, 2012, now U.S. Pat. No. 8,920,484, as a U.S. national stage application under 35 USC § 371 of International Application No. PCT/EP2010/057401, filed May 28, 2010, claiming priority to United Kingdom Patent Application No. 0909319.6, filed May 29, 2009, and to U.S. Provisional Application No. 61/182,263, filed May 29, 2009, each of which is incorporated by reference in its entirety into this application.

FIELD OF THE INVENTION

This invention relates to a transluminal delivery system for a self-expanding luminal prosthesis, the system comprising an inner catheter component and a retractable sheath to surround the component thereby to define an angular space to receive the prosthesis, the component exhibiting an anti-sliding component, for abutting a luminal surface portion of the prosthesis to restrain the prosthesis from sliding with the sheath, and relative to the inner catheter, while the sheath retracts relative to the prosthesis to release the prosthesis progressively into the target bodily lumen.

The invention also relates to a method of connecting a radially inwardly compressed self-expanding stent to an inner catheter within the lumen of the stent so that when the stent is delivered to a stenting site, the stent is retained against axial movement, relative to the inner catheter, while a sheath disposed radially outside the stent and imposing a radially inwardly compressive effect on the stent is retracted proximally along the length of the stent, to release the stent radially outwardly, distal of the distal end of the sheath.

The invention also relates to a method of building an assembly of a transluminal delivery system and a self-expanding prosthesis for a bodily lumen, the system comprising an inner catheter and a retractable sheath that surrounds the prosthesis and may be retracted to release the prosthesis, progressively, into the bodily lumen, the inner catheter including an anti-sliding component that occupies a lumen of the prosthesis and restrains the prosthesis from sliding with the sheath while the sheath retracts.

STATE OF THE ART

Transluminal delivery systems for self-expanding stents are disclosed in Applicant's WO 2005/030092, in WO 2000/71058 of Scimed Life Systems Inc. and in WO 2009/033066 of Cook Inc. These WO publications show components within the lumen of the stent that inhibit sliding of the stent with the sheath when the sheath is retracted, relative to the inner catheter, progressively to release the stent from the delivery system. Further disclosures of structures that engage with the luminal surface of a stent housed in a catheter delivery system are to be found in U.S. Pat. Nos. 7,172,618, 5,702,418, 6,576,006, 6,620,191, 7,473,271 and 7,241,308.

With stent delivery systems being required to deliver ever more sophisticated stents to ever more challenging locations within the body of a patient, the engineering demands on the delivery systems have never been higher. The ideal delivery system inner catheter restrains the stent from sliding proximally with the sheath surrounding the stent without imposing any local stress concentrations on any particular part of the stent. Ideally, the inner catheter pushes evenly, all over the maximum possible surface area of the stent being restrained. Good inner catheters are therefore those that can accommodate local variations in inside diameter of the compressed stent within its sheath, and which abut the luminal surface of the sheath throughout the length of the sheath. There should be minimal likelihood of any damage to the stent during the assembly of the stent with its delivery system and the delivery system as such should be simple and economical in construction and operation. To an extent, these design objectives are incompatible. The present invention aims to bring to an unprecedentedly high level the successful compromise of the conflicting design objectives.

SUMMARY OF THE INVENTION

In a nutshell, the underlying concept of the present invention is to provide on the inner catheter an anti-sliding component that can be slid axially into position in the lumen of the stent and which has a capacity to swell radially so that the radial thickness during the building of the assembly may be less than the radial thickness of the anti-sliding component during retraction of the sheath. In one simple realization of the inventive concept, an anti-sliding component in the form of a sleeve is stretched axially, to reduce its radial thickness while the stent is crimped down onto the reduced thickness anti-sliding component. A sheath is introduced around the crimped stent and then, after that, the axial tension on the anti-sliding component is released, allowing the material of the anti-sliding component to relax, and the length to reduce, with consequent swelling of the radial thickness of the anti-sliding component. Any such swelling can vary locally, being at its greatest where the internal diameter of the annular stent is locally larger than average. Analogously, where the internal diameter of the stent is somewhat smaller than average, the capacity for local radially outwardly swelling of the anti-sliding component is rather more confined and occurs to a rather lesser extent. The consequence is that the anti-sliding component presses against more or less the entire axial length of the luminal surface of the stent, regardless of whether that luminal surface exhibits local variations in luminal diameter.

There are, however, other embodiments. Consider, for example, an inner catheter that carries, coaxially on its abluminal surface, a cylindrical braid with a very small radial thickness and which is bonded to the inner catheter within its lumen, but only at one end of the braid. This composite inner catheter is then introduced axially into the lumen of the stent, with the braid entering the stent lumen with the bonded portion of its length at the leading end, that enters the stent lumen first. Thus, as the inner catheter is advanced along the length of the stent lumen, the bonded leading end of the braided cylinder pulls the remaining length of the braid cylinder into the stent lumen. The braid is under mild lengthwise tension, to the extent there is any frictional drag, as the inner catheter is advanced into the stent lumen. Much later, when the stent is being deployed, if the bonded portion of the braid is more proximal in relation to the stent than the unbonded remainder of the length of the braid, then any friction-induced tendency of the stent to slide proximally relative to the inner catheter will impose an endwise compressive stress on the braid cylinder, with the consequence that it will tend to "ruck up" or assume a crumpled form, which thereby "locks up" the gap between the inner catheter and the stent and resists any further proximal movement of the stent relative to the inner catheter shaft.

A striking technical effect of such a "lock up" concept is that, the more shear stress is imposed on the anti-sliding element by the stent, the more the element locks up, to resist that stress. In other words, the stresses imposed by the anti-sliding element on the stent are only as high as they need to be, to stop the stent sliding relative to the inner catheter.

A similar effect can be engineered, by endowing the abluminal surface of the inner catheter with a plurality of cantilevered filaments with good column strength that extend radially outwardly from the inner catheter shaft to give it a velvet or flock appearance. When one advances the flocked inner catheter into the stent lumen, from one end of the stent lumen, then the end of the stent first encountered by the filaments will push the filaments back so that they trail each from a leading end fixed to the inner catheter that is advancing into the lumen of the stent. Later, when the sheath is retracted to release the stent, and the stent tends to be entrained and carried proximally with the sheath, the free ends of the filaments will press against the luminal surface of the stent and the anchorage of the respective opposite ends of each filament, on the inner catheter, proximally of the free ends of the filaments pressing against the stent, will restrain any further proximal movement of the stent relative to the inner catheter. One can imagine each of the filaments functioning as a miniature pawl, with a tendency to resist sliding of the stent relative to the inner catheter that benefits from a high column strength in each filament.

Preferably, the anti-sliding component should be arranged so that it works to greatest effect near the distal end of the stent, as the sheath surrounding the stent is pulled back proximally, so that the stent, in general, suffers a degree of lengthwise axial tension during such withdrawal. Such preferential effect at the distal end might be engineered by arranging for the anti-sliding component to have an inherently larger diameter near the distal end of the stent than it exhibits closer to the proximal end of the stent.

The invention may be applied in a wide variety of delivery systems where it is desired to deliver an implant such as a stent, filter, stent graft or stent with an integrated heart valve via a catheter with a high deployment accuracy.

BRIEF DESCRIPTION OF THE DRAWINGS

For a better understanding of the invention, and to show more clearly how the same may be carried into effect, reference will now be made, by way of example, to the accompanying drawings, in which.

DETAILED DESCRIPTION

Figure 1:
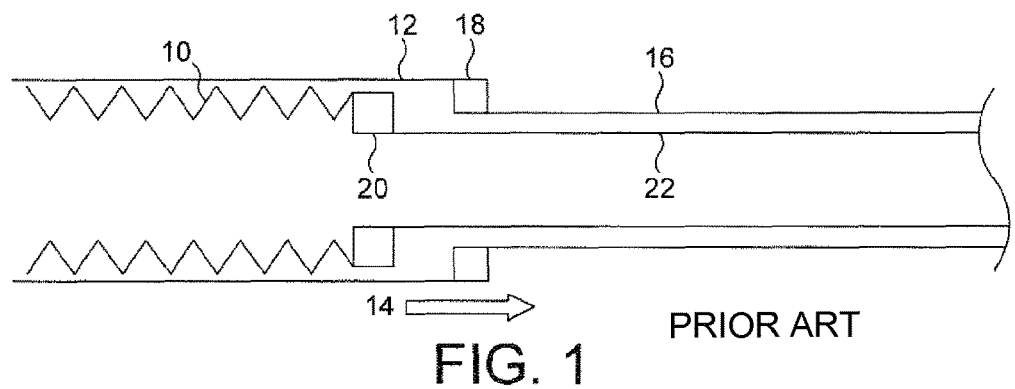
FIG. 1 is a longitudinal diametral section through a "classic" delivery system to release a self-expanding stent.

The schematic drawing of FIG. 1 shows a stent 10 that has been radially crimped to a small diameter for advancement along a lumen to a stenting site within the body of a patient. To release the stent into the bodily lumen a sheath 12 that surrounds the stent and confines it radially is pulled back proximally in the direction of arrow 14 using a pulling device 16 such as a pull tube or pull wire that runs all the way back to the hand unit (not shown) at the proximal end of the transluminal catheter delivery system. Typically, there is some sort of bond, such as with a collar 18, that connects the pulling element 16 with the sheath 12 that surrounds the stent.

Absent any other structure, then any proximal movement of the sheath 12 will carry the stent with it because the stent is a self-expanding stent and so is continuously pressing on the luminal surface of the sheath 12. To stop the stent 10 moving proximally with the sheath 12, it has been conventional to employ an annular element 20 that can conveniently be termed a "stopper." The stopper element 20 also runs back to the not-shown hand unit, through a shaft 22 that will of course be in endwise compressive stress during the time period when the sheath 12 is being retracted and the stopper 20 is required to stop the stent moving proximally with the sheath 12. By contrast, the pulling element 16 during this time period will be in endwise tensile stress.

One can see immediately from FIG. 1 that the stopper annulus 20 carries all of the load that the stent 10 imposes on the catheter shaft element 22 that finds itself in endwise compressive stress during stress deployment. Thus, portions of the structure of the stent 10 that are immediately distal of the stopper annulus 20 are liable to suffer greater concentrations of stress than portions of the stent 10 up near the distal end of the stent, remote from the stopper annulus 20. This is not ideal. Ideally, the stresses imposed on the stent during release of the stent should be shared homogeneously and equally by all portions of the structure of the stent.

Figure 2:
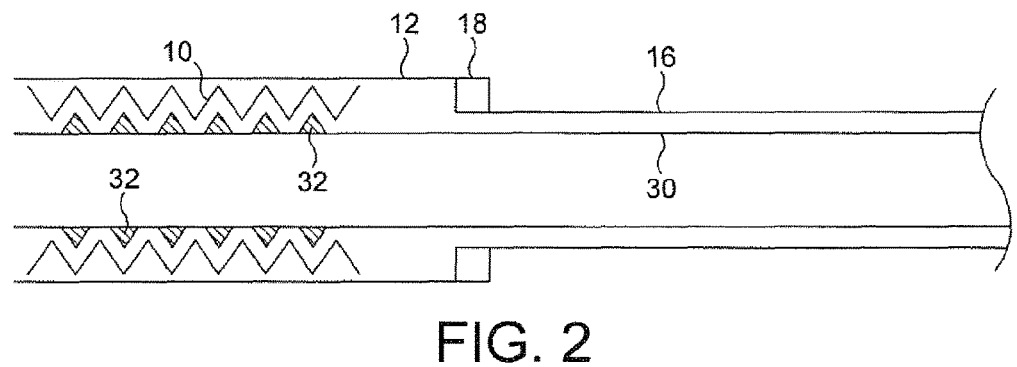
FIG. 2 is a longitudinal diametral section through a delivery system as in FIG. 1, but including an inner catheter with an anti-sliding component.

Turning to FIG. 2, the stent 10 is the same and the outer sheath 12 is the same and the pulling element 16 is the same but the inner catheter that will be in compressive stress while the stent is being released is in the form of an elongate tube 30 that extends through the lumen of the stent 10. On the abluminal surface of the inner catheter tube 30 there is provided a plurality of protuberances 32 that can engage with the luminal surface of the crimped stent 10. Contemplated is to place the inner catheter with the protuberances inside the lumen of the stent 10 before crimping the stent down onto the protuberances and surrounding the crimped stent with the sheath 12.

Clearly, this assembly technique can bring advantages relative to the basic system of FIG. 1, especially in the case of stents of great length and great flexibility.

Figure 3:
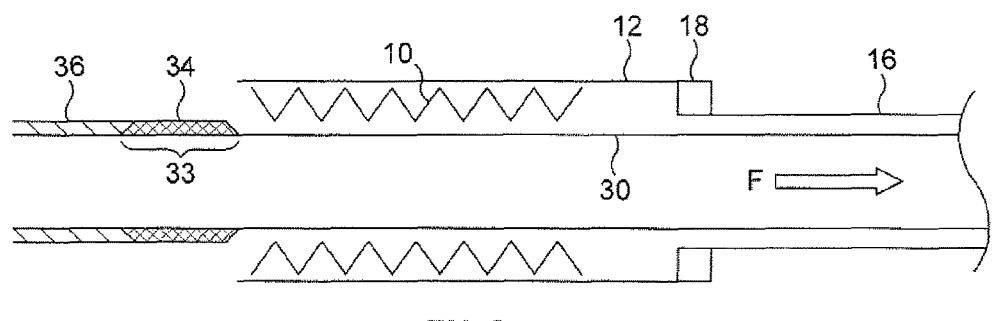
FIGS. 3, 5, 6 and 8 to 12 are longitudinal diametral sections like FIGS. 1 and 2, with an inner catheter that exhibits an anti-sliding component in accordance with the present invention.

Looking now at drawing FIG. 3, we see the same arrangement of stent 10, sheath 12 and pulling element 16, but inside the lumen of the stent is an inner catheter 30 moving from left to right in the drawing as indicated by arrow F. In fact, the inner catheter 30 is being installed in the lumen of the stent 10, to create an assembly of inner catheter, stent and sheath 12 for incorporation in the catheter system for delivering the stent 10.

The inner catheter 30 has an abluminal surface to which is bonded in length portion 33 an end portion 34 of a cylindrical braided element 36 that fits snugly around the external diameter of the inner catheter shaft 30. Most of the length of the braid 36 is free to slide on the abluminal surface of the inner catheter 30, the exception being in the end zone 33. It will be appreciated that when one pulls the inner catheter 30 from left to right in FIG. 3, through the lumen of the stent 10, in the direction of arrow F, the leading portion 34 of the braid 36 can be pulled to a position adjacent the proximal end of the stent and the collar 18 between the stent sheath and the pulling member 16. This will leave the sliding portion of the length 36 of the braid inside the stent lumen, and it is arranged for the braid to be a relatively snug fit between the inner catheter 30 and the luminal surface of the stent 10.

Figure 6:
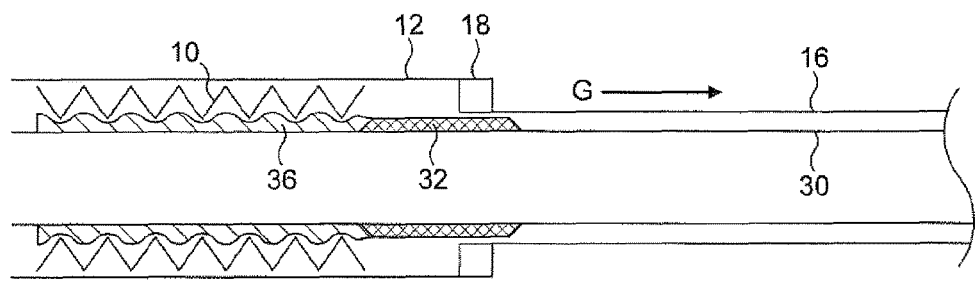

Now, turning to FIG. 6, we can see what happens when it is time to deploy the stent and the pulling member 16 is pulled proximally, in the direction of arrow G relative to the inner catheter 30. The stent 10 at first follows the proximal movement of the sheath 12 but this will have the effect of "rucking" the slidable braid 36 which, in consequence, will tend to "pile up" in any interstices available to it, within the luminal surface of the stent 10. Any such piling up, or departure from a cylindrical abluminal surface of the braid 36, will have a braking effect on the incipient proximal movement of the stent 10, because the braid 36 cannot slide proximally to any extent, blocked as it is by the fixation of the proximal end of the braid 36, to the inner catheter 30, in length portion 33. In this way, the stent 10 can be released without any significant proximal sliding relative to the inner catheter 30.

Although FIG. 6 shows the length portion 33 of the inner catheter at the proximal end of the stent, it is also contemplated to provide it up near the distal end of the stent lumen. Indeed, it is contemplated to provide a plurality of short lengths of braid, spaced along the inner catheter in the stent lumen, each tethered to the inner catheter at the proximal end of each such braid length.

It is conventional to use a cylindrical braid when a degree of "springiness" is desired, such as in the child's toy called the "Chinese Finger" or a self-expanding stent after Wallsten. Here, however, one is looking for a braid that has some capability to crumple or concertina, which is almost the opposite of the quality of springiness.

As ever, materials and dimensions are chosen deliberately on the basis of optimizing fitness for purpose. Here, one will contemplate the ideal number of filament crossing points per unit of axial length of the cylindrical braid and the possibility to blend different materials in the filament weave. One possibility is to incorporate filaments of polyurethane as damping filaments. A homogeneous or heterogeneous mixture of filaments selected from steel, nitinol or other alloys may form the braid, and heat-treating of some or all of these materials may be used to desirably tune the mechanical properties of the braid. The braid itself may be enclosed in a very thin polymer matrix, for example polyurethane. Possibly, it will be effective to use filaments of non-circular cross section, rough-surfaced or with corners (square or hexagon cross-section, for example) to enhance frictional engagement with the stent and inner catheter during stent release. It may be effective to roughen the abluminal surface of the inner catheter beneath the braid.

Figure 8:
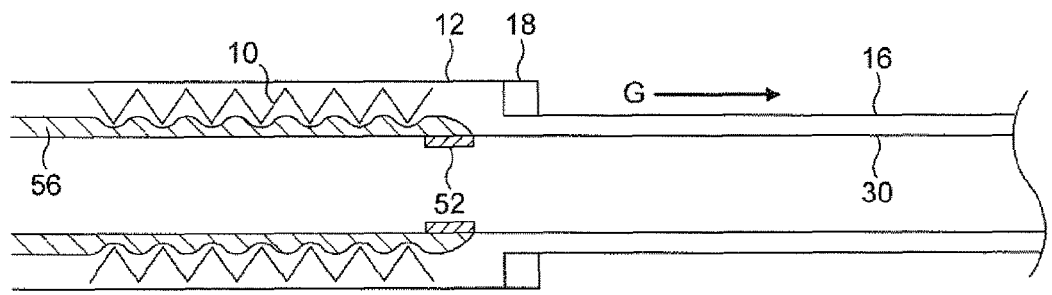

The inventor contemplates that braid lengths of as little as 5 mm (or even less) may be fully effective to accomplish the desired effect. That is to say that the axial length of the unbonded portion of the braid (not including the portion which is bonded to the inner catheter 30) need only be 5 mm in length, possibly even shorter, depending on the particular application for which it is being used. The same will apply to other non-braided tubular anti-sliding components and sleeves, such as the sleeve 50 of FIG. 8.

Indeed, as the length of such braided and non-braided sleeves is increased, so too is the extent to which the sleeves will nick up or crumple, as well as the extent to which their thickness will increase, as the unbonded portions slide along the abluminal surface of the inner catheter 30. In certain circumstances, where the anti-sliding sleeve is of significant length, this can generate undesirably large radial forces acting radially inwardly on the inner catheter 30 and radially outwardly on the surrounding stent 10 and sheath 12. Where the radial forces are too large, retraction of the sheath 12 and proper positioning and placement of stent 10 may be inhibited, and there is a risk of damaging one or more of the inner catheter 30, stent 10 or sheath 12. Such consequences are counter to the objective of spreading the compressive forces which hold the stent 10 in position on the inner catheter 30 along the axial length of the stent 10, rather than having concentrated forces at the location of a stopper annulus 20 as described in relation to FIG. 1 above, when the sheath 12 is retracted.

To this end, a shorter length of anti-sliding sleeve is preferred, and it is furthermore proposed to provide two or more of the anti-sliding sleeves along the length of the inner catheter 30 within the lumen of the stent 10, depending on the length of the stent 10 to be delivered and the forces involved. Currently, the use of two or three anti-sliding sleeves is preferred, for most stent delivery applications. Of course, the anti-sliding sleeves may all be of the same configuration, or different lengths and types of sleeves may be used at different positions along the length of the inner catheter 30 within the lumen of stent 10. For example, a mixture of braided and non-braided sleeves may be used in the same transluminal catheter delivery system. Different materials or combinations of materials may be selected for use in each individual anti-sliding sleeve, as appropriate.

Figure 4:
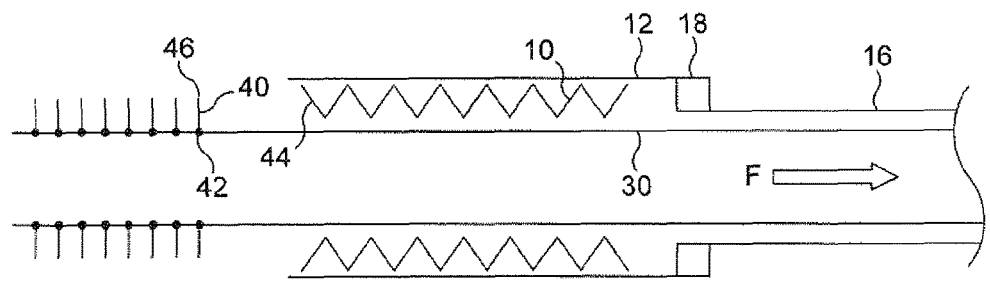
FIGS. 4 and 7 are longitudinal diametral sections like FIGS. 1 and 2, with an inner catheter that exhibits anti-sliding filaments.

Turning to FIG. 4, there is shown an alternative way of reducing the likelihood of the stent 10 sliding on the abluminal surface of the inner catheter 30, whereby the abluminal surface of the inner catheter 30 is equipped with a multitude of filaments 40 that extend radially outwardly from a fixed end 42 of each of the filaments 40, respectively fixed to the abluminal surface of the inner catheter 30. As the catheter 30 is pulled through the lumen of the stent 10, as described above in relation to FIG. 3, and as indicated again by arrow F, the distal end 44 of the stent will press against each of the arriving filaments 42 and will cause them to lie down more parallel to the length direction of the inner catheter, with the cantilevered free end 46 of each filament located distally of the fixed end 42 by the length of the filament 40.

Figure 7:
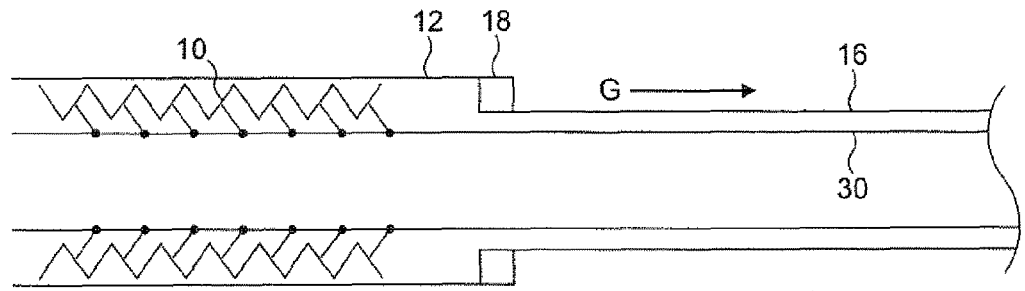

Turning to FIG. 7, we see how a tensile stress on the pulling element 16, causing it to move in the direction of arrow G, and tending to drag the stent 10 with it, will prompt engagement (in the manner of a pawl) between the free end 46 of many, or most, or all of the filaments 40 with a surface portion of the luminal surface of the stent 10. Any such abutment will have the natural effect of resisting any proximal sliding of the stent 10 relative to the inner catheter 30. Any such resistance to sliding, however, will have no inhibitory effect on the radial expansion of the distal end of the stent 10, as the sheath 12 slides progressively and proximally away from the stent 10. Furthermore, once the stent is deployed, the filaments 40 present no obstacle to proximal withdrawal of the inner catheter from the deployed stent 10 and the bodily lumen in which the delivery catheter has been advanced to the stenting site.

Figure 5:
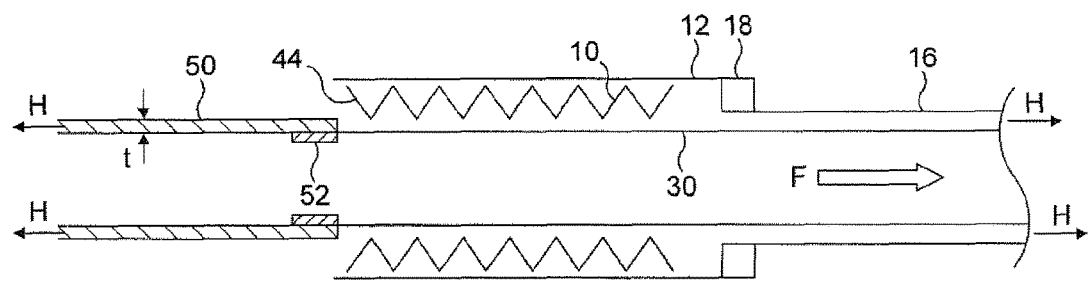

Turning now to a third embodiment, as shown in FIG. 5, the inner catheter 30 is provided with a sleeve 50 that is, in general, freely slidable on the abluminal surface of the inner catheter 30. As an exception, in a small portion 52 of the length of the inner catheter 30, there is an adhesive bond between the catheter 30 and the slidable jacket/sleeve 50. In this embodiment, an endwise tensile stress, represented by arrows H, is imposed on the sleeve 50 prior to any pulling of the inner catheter 30 through the lumen of the stent 10, as represented by arrow F. The imposition of the endwise tensile stress has the effect of reducing the radial thickness t of the sleeve 50. This reduced radial thickness facilitates progress of the inner catheter shaft 30 axially through the lumen of the stent 10. The catheter is advanced until the short length portion 52, where the sleeve 50 is bonded to the catheter 30, arrives at a position adjacent to the proximal end of the stent 10. Once the tensioned sleeve 50 lies within the stent lumen, and the stent is safely confined within the sheath 12, the endwise tension can be released, allowing the radial thickness t of the sleeve 50 to increase and any such thickness increase will manifest itself as an expansion, locally, of portions of the sleeve, into interstices of the luminal surface of the stent 10. See FIG. 8. Any such form fit between the abluminal surface of the sleeve 50 and the luminal surface of the stent 10, allied to the bonding of the sleeve 50 to the inner catheter 30, will have the effect of acting as a brake on any tendency of the stent 10 to move proximally with the sleeve 12, relative to the inner catheter 30.

If desired, the abluminal surface of the inner catheter of the third embodiment (and even the abluminal surface of the braid of the first embodiment) could be rendered filamentous, to take advantage of the idea of the second embodiment as well.

Figure 9:
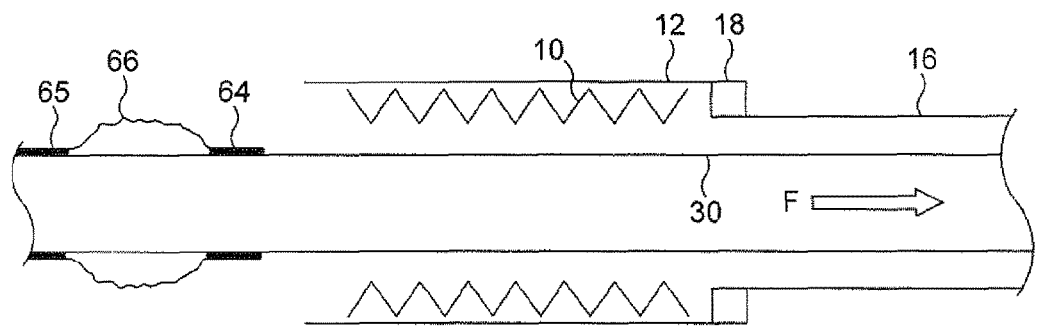

Another embodiment of the invention is shown in FIG. 9. This embodiment is somewhat similar to that of FIG. 3, in that the inner catheter 30 has an abluminal surface to which is bonded a proximal end portion 64 of a cylindrical element 66. The cylindrical element 66 is made of a flexible tubing and fits loosely around the external diameter of the inner catheter shaft 30. It is again bonded at a distal end portion 65. However, the locations at which end portions 64 and 66 are bonded to the inner catheter 30 are selected such that an intermediate unbonded length of the cylindrical element 66 lying between the end portions is greater than the distance between the locations at which the end portions 64 and 66 are bonded, so that the unbonded length is to a certain extent free to slide on the abluminal surface of the inner catheter 30.

It will be appreciated that the arrangement of FIG. 9 allows the cylindrical element 66 to nick up in either direction, meaning that the inner catheter 30 can be used for urging a surrounding stent 10 in both directions. This effect can be utilized to advantage both in manufacturing and use of a transluminal catheter delivery system.

Although it has been proposed to crimp the stent 10 and load the stent 10 into a sheath 12, prior to then drawing the inner catheter 30 axially into the delivery system within the lumen of the stent 10 (as denoted by arrows F in FIGS. 3, 4 and 5), such a method presents additional complexity.

Specifically, after crimping the stent 10 to its reduced diameter, one has first to load the stent 10 into the sheath 12. One way to do this is to push the stent 10 axially from within the crimping device into an adjacently disposed and aligned sheath, for example using a pusher configured like the inner catheter 30 of FIG. 2. Such a pusher then has to be withdrawn from inside the lumen of the stent 10 so that the inner catheter 30 having the anti-sliding component can be inserted proximally (in the direction of arrows F) into the lumen of stent 10 within sheath 12.

It would be preferable, instead, to crimp the stent 10 down directly onto the inner catheter 30 having the anti-sliding component. The inner catheter 30 with the anti-sliding component may then be used to push the crimped stent 10 into the sheath 12, without needing to use a separate pusher or to carry out a separate step of inserting the inner catheter 30 with the anti-sliding sleeve into the lumen of stent 10 after it has been installed in the sheath 12.

Although this is possible with the inner catheters 30 of FIGS. 3 to 8, there is a drawback in that the stent 10 then has to be pushed distally, from the proximal opening of the sheath 12, along the whole length of the sheath 12, until the distal end of the stent 10 is at or near to the distal end of the sheath 12, ready for deployment by proximally retracting the sheath 12 (in a transluminal catheter delivery system in which the stent to be deployed is located near the distal end of the catheter and the sheath is retracted proximally). This is necessary, since the inner catheters 30 of these Figures have only one-directional pushing ability. Such a process is impractical, however, in many systems in which the retractable restraining sheath is significantly longer than the stent to be deployed. In some systems, the retractable sheath extends along substantially the whole length of the catheter, rather than having a separate pulling element 16, whereas the stent is located only along a relatively short distal portion of the catheter.

It is therefore contemplated to use the inner catheter 30 of FIG. 9 so that, in manufacture of the transluminal catheter delivery system, the stent 10 can be crimped down onto the inner catheter 30, and the inner catheter 30 can then be used to pull the stent 10 into the aligned sheath 12 from the distal end of the sheath 12, only for a distance substantially equal to the length of the stent, even if the sheath 12 is significantly longer than the stent 10 to be deployed. This is possible as the anti-sliding sleeve 66 is fixed at both ends, and so will crumple (nick up) towards the bonded distal end portion 65 of the sleeve 66, thereby engaging with the inner lumen of the crimped stent to enable the inner catheter 30 to urge the stent proximally into the distal end of an aligned sheath 12. The inner catheter then remains within the lumen of the stent 10 and the sheath 12, as the inner catheter of the delivery system.

In order to deploy the stent 10 using such a system, the sheath 12 is then retracted proximally by pulling on pulling element 16, which places the inner catheter 30 in compression. The sheath 12 tends to draw the stent 10 proximally, which in turn causes the sleeve 66 to ruck up towards the bonded proximal end portion 64 of the sleeve 66. The sleeve 66 thereby engages the inner lumen of the stent 10, as in the embodiments already described, to effectively push the stent 10 against the sheath retraction force and hold the stent 10 in place as it expands upon release from the sheath 12. In this way, as the stent 10 is deployed, the interaction between the rucked zone and the luminal surface of the stent 10 prevents significant proximal sliding relative to the inner catheter 30, and allows precise deployment.

In this embodiment, the cylindrical element 66 is advantageously PET tubing so that the end portions 64 and 65 may be secured on the inner catheter by heat-shrinking while the sliding portion remains free to translate and crumple (nick up) as required.

Regarding the engagement between the anti-sliding sleeve component 66 and the inner lumen of the surrounding stent 10, as with the anti-sliding sleeves 36, 50, 76 of the other embodiments disclosed herein, it has been contemplated that where the anti-sliding sleeve is nicked up the sleeve material or braids may inter-engage with the interstices of the sent 10. However, for many stents, the interstices are not sufficiently open, with the stent in the crimped configuration, to allow for such inter-engagement. Indeed, for stents which are laser cut from a Nitinol tube, there are virtually no interstices in the stent structure in the crimped, reduced-diameter configuration. The engagement between the anti-sliding components and the stent inner luminal surface is, therefore, in most cases, simply a frictional engagement. By selecting suitable materials for the anti-sliding sleeves, a secure frictional engagement can be achieved. Moreover, by selecting a suitable material for the anti-sliding sleeve, the anti-sliding sleeve can present a "soft" bed onto which the stent 10 can be crimped, without damaging the stent 10 or any stent coating. By using a suitably pliable (soft) material, the frictional engagement between the anti-sliding component and the stent luminal surface can also be enhanced. If desired, an outer polymeric sleeve could be incorporated in or provided on the outside of a braided sleeve, the braided sleeve providing the material resilience to present a crumpling action and the sleeve improving the frictional engagement between the braided sleeve and the stent luminal surface (as compared to the frictional engagement between only a braided layer and the stent luminal surface). Incorporating a braided sleeve in a thin PUR matrix is contemplated.

Figure 11:
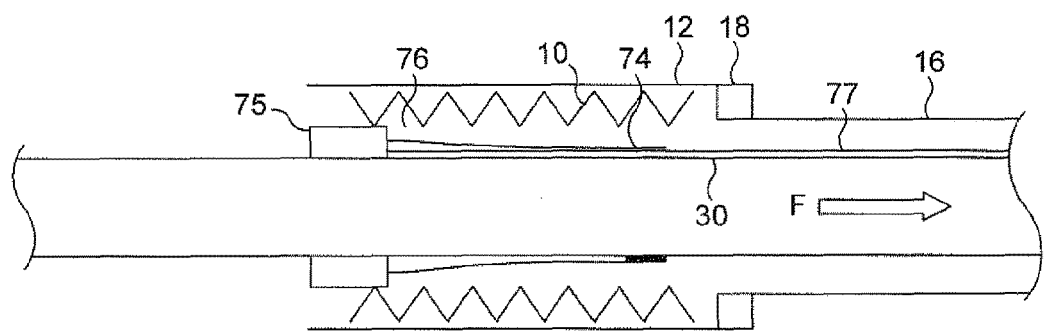
Figure 12:
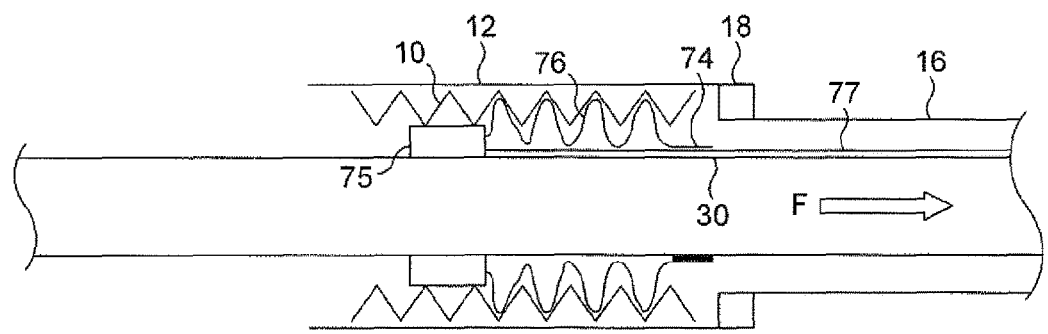

A further embodiment of the invention is now described with reference to FIGS. 10, 11 and 12. This embodiment may be useful in situations where it is desired to have separate control of motion of the stent and the anti-sliding action of the anti-sliding component. This embodiment is also advantageous in that it allows the anti-sliding sleeve to be engaged with the inner lumen of the stent 10 without any initial retraction or movement of the stent 10 with the sheath 12, which is needed to a small but generally insignificant degree with the above-described embodiments. It is, though, preferred to avoid any positional variation of the stent 10 relative to the inner catheter 30 during deployment as far as possible, as this improves precision of stent placement.

Figure 10:
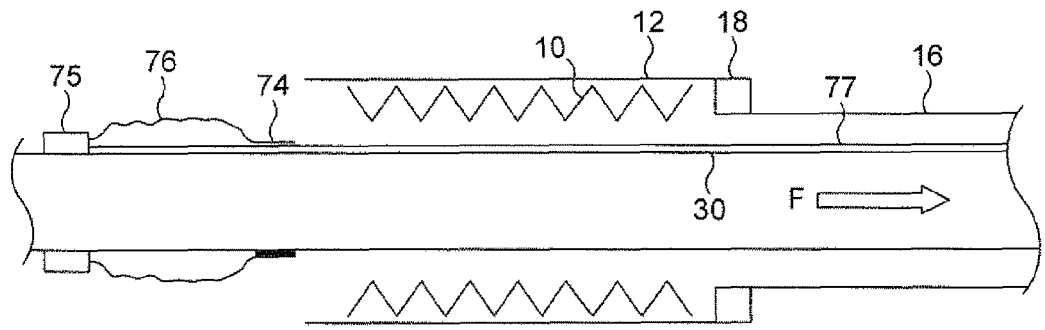

In this embodiment, as shown in FIG. 10, a loose sleeve 76 is positioned about the inner catheter 30 and bonded to the inner catheter 30 at a proximal portion 74. The sleeve may be flexible tubing, braided wire or a composite structure of either. The distal portion is attached to an annular slider 75, which is centered on but also free to slide on the inner catheter 30. The intermediate portion between proximal and distal portions is otherwise unattached to the inner catheter. Running proximally from the slider 75 underneath sleeve 76 is a pull element 77 which is also free to slide and traverses bonded portion 74 without impedance, for example by means of an aperture or slit.

Stent 10 may be loaded onto inner catheter 30 by crimping the stent 10 down onto the inner catheter 30 slider 75 and sleeve 76, as for the embodiments described above. The stent remains at this stage substantially freely movable relative to the inner catheter. Such a configuration may be seen in FIG. 11.

When, during deployment of the stent 10, the correct position of the stent 10 is reached for it to be released from the sheath 12, proximal tension is applied to the pull element 77 causing the slider 75 to travel proximally relative to stent, catheter and bonded proximal portion 74 of the sleeve 76. As the sleeve 76 is compressed longitudinally between slider 75 and bonded proximal portion 74, it will expand in radial extent, for example by rucking up or crumpling, as explained with reference to the embodiments described above, to engage with the luminal surface of the stent 10. The more tension that is applied to the pull element 77, the closer the slider 75 approaches bonded proximal portion 74, and the greater the degree of interaction between the sleeve 76 and the luminal surface of the stent 10. Motion of the stent relative to the catheter will tend to strengthen this interaction further, in analogous ways to those described above with reference to the other embodiments. In this way, the stent 10 can be restrained on demand from motion relative to the catheter 30 by actuation of the pull element 77. Such a configuration may be seen in FIG. 12.

In some applications, it may even be desirable to make the process reversible, and allow the pull element 77 to have sufficient column strength to translate the slider 75 in the distal direction, returning the sleeve 76 to its previous uncrumpled configuration and relieving the stent 10 from the radial restraining force.

In this embodiment, the sleeve 76 is advantageously PET tubing while the slider can be constructed as a PEBAX tube riding on an inner PI tube. Alternatively, a metal braid may be used as a sleeve, as in the embodiment of FIG. 3. In general, it may be useful to include features that increase levels of friction between the abluminal surface of the inner catheter and any portion of an anti-sliding component that is slidable on that surface. That might take the form of a roughening of that abluminal surface, a roughening of any luminal surface of the slidable component, or both.

In connection with the embodiments described above, a stent receiving element may be provided on a portion of the unbonded sliding portion of the sleeve. Such is shown at the distal end of the sleeve 76 in FIG. 11, in which the slider or slide ring 75 is provided with an enlarged diameter as compared to the diameter of the sleeve 76. An enlarged diameter element of this kind may also be provided to the anti-sliding sleeves of the other embodiments, regardless of whether they include a sliding ring. The enlarged diameter element is preferably of a relatively soft material, to avoid damaging the stent 10 or inner catheter 30. The receiving element serves to first receive the inner lumen of the stent 10, as stent 10 is crimped down onto the inner catheter 30 and anti-sliding sleeve 76. As such, the stent 10 is first crimped down onto the receiving element before coming into engagement with the anti-sliding sleeve 76. After the stent 10 engages with the receiving element 75, the stent 10 may be moved towards a bonded portion of the anti-sliding sleeve 76, here proximally in the direction of arrow F in FIG. 10. This causes the unbonded portion of the anti-sliding sleeve 76 to crumple between the receiving element 75 and the bonded portion 74, ensuring a uniform nicking up along the length of the unbonded portion of the anti-sliding sleeve. The stent 10 may then be further crimped onto the inner catheter to further reduce its diameter and bring it into engagement with the rucked up anti-sliding sleeve. Although described as a two-stage crimping process, the procedure may be completed in a single movement using an appropriate crimping device and effecting a longitudinal movement of the inner catheter 30 relative to the stent 10, once the stent is engaged with the receiving element 75.

Such receiving elements are also useful, even if the above steps are not taken during the manufacturing and assembly process, as they allow the nicking or crumpling behavior of the anti-sliding sleeve to be more accurately predicted and controlled, by guaranteeing that the sleeve 76 will crumple in the region between the receiving element 75 and the fixed portion 74 of the anti-sliding sleeve 76. Without a receiving element 75, portions of the anti-sliding sleeve 76 which were not in good contact with the stent 10 may not get nicked up during retraction of the sheath 12 (in the embodiments not using a pull element 77), or may not get nicked up evenly or uniformly along the length of the antisliding sleeve. Receiving element 75 is therefore useful in these respects.

An important part of the routine work of stent delivery system designers is to select optimum materials for individual component parts of stent delivery systems. The present invention is no exception to this general rule. For the skilled reader of this specification, choice of materials is a matter of background knowledge and routine expertise. The skilled reader will be able readily to appreciate how the present inventive concept allows assembly of a catheter-type, transluminal stent delivery system that has minimal passing diameter and maximal management of the movement of the stent during release of the stent from the system, with minimal occurrence of unpredictable stress overloading of any part of the material of the stent being deployed.

What is claimed is:

1. A transluminal delivery system for deploying a stent in a patient, comprising:
    a retractable sheath positioned over the stent; and
    an inner catheter positioned through a lumen of the stent, the inner catheter comprising: a tubular portion having an abluminal surface; and
        a cylindrical braid element positioned over the abluminal surface of the tubular portion, the cylindrical braid element comprising:
            an inner surface contacting the abluminal surface of the tubular portion over an entire length of the cylindrical braid element;
            a proximal region bonded to the abluminal surface of the tubular portion; and
            an unbonded distal end slidably disposed on the abluminal surface of the tubular portion.

2. The transluminal delivery system according to claim 1, wherein the proximal region of the cylindrical braid element is adjacent a proximal end of the stent prior to deployment of the stent.

3. The transluminal delivery system according to claim 2, further comprising a collar connected to the retractable sheath and a pulling member, wherein a proximal end of the proximal region of the cylindrical braid element is adjacent the collar prior to deployment of the stent.

4. The transluminal delivery system according to claim 2, wherein a distal end of the cylindrical braid element is within the lumen of the stent prior to deployment of the stent.

5. The transluminal delivery system according to claim 1, wherein the cylindrical braid element is a first braid element, and wherein the inner catheter further comprises a second braid element having a second proximal region bonded to the abluminal surface of the tubular portion, and a second unbonded distal end slidably disposed on the abluminal surface of the tubular portion.

6. The transluminal delivery system according to claim 1, wherein the cylindrical braid element comprises a plurality of filaments formed from at least two different materials.

7. The transluminal delivery system according to claim 6, wherein one of the at least two different materials is polyurethane.

8. The transluminal delivery system according to claim 1, wherein the cylindrical braid element is enclosed in a thin polymer matrix.

9. The transluminal delivery system according to claim 1, wherein the cylindrical braid element comprises a plurality of filaments having a non-circular cross-section.

10. The transluminal delivery system according to claim 1, wherein the abluminal surface of the tubular portion of the inner catheter is roughened.

11. The transluminal delivery system according to claim 1, wherein the cylindrical braid element distal of the proximal region is 5 mm.

12. A transluminal delivery system for deploying a stent in a patient, comprising:
    a retractable sheath positioned over the stent; and
    an inner catheter positioned through a lumen of the stent, the inner catheter comprising:
        a tubular portion having an abluminal surface; and
        two or more cylindrical braid elements positioned over the abluminal surface of the tubular portion, each of the two or more cylindrical braid elements comprising:
            an inner surface contacting the abluminal surface of the tubular portion over an entire length thereof;
            a proximal region bonded to the abluminal surface of the tubular portion; and an unbonded distal end slidably disposed on the abluminal surface of the tubular portion.

13. The transluminal delivery system according to claim 12, wherein the two or more cylindrical braid elements comprise a first cylindrical braid element, a second cylindrical braid element, and a third cylindrical braid element.

14. The transluminal delivery system according to claim 13, wherein the proximal region of the first cylindrical braid element is adjacent a proximal end of the stent prior to deployment of the stent.

15. The transluminal delivery system according to claim 14, further comprising a collar connected to the retractable sheath and a pulling member, wherein a proximal end of the proximal region of the first cylindrical braid element is adjacent the collar prior to deployment of the stent.

16. The transluminal delivery system according to claim 13, wherein a distal end of each of the first, second, and third cylindrical braid elements is within the lumen of the stent prior to deployment of the stent.

17. The transluminal delivery system according to claim 12, wherein at least one of the two or more cylindrical braid elements comprises a plurality of filaments formed from at least two different materials.

18. The transluminal delivery system according to claim 17, wherein one of the at least two different materials is polyurethane.

19. The transluminal delivery system according to claim 12, wherein at least one of the two or more cylindrical braid elements is enclosed in a thin polymer matrix.

20. The transluminal delivery system according to claim 12, wherein the abluminal surface of the tubular portion of the inner catheter is roughened.

* * * * *